United States Patent
Graf et al.

(10) Patent No.: US 8,791,532 B2
(45) Date of Patent: Jul. 29, 2014

(54) SENSOR MOUNTED IN FLIP-CHIP TECHNOLOGY ON A SUBSTRATE

(75) Inventors: Markus Graf, Zürich (CH); Werner Hunziker, Stäfa (CH); Franziska Brem, Küsnacht (CH); Felix Mayer, Stäfa (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 13/498,371

(22) PCT Filed: Nov. 18, 2009

(86) PCT No.: PCT/CH2009/000367
§ 371 (c)(1),
(2), (4) Date: Jun. 22, 2012

(87) PCT Pub. No.: WO2011/060558
PCT Pub. Date: May 26, 2011

(65) Prior Publication Data
US 2012/0267731 A1    Oct. 25, 2012

(51) Int. Cl.
*H01L 29/84* (2006.01)
*H01L 21/02* (2006.01)
*H01L 21/56* (2006.01)
*G01L 19/14* (2006.01)
*H01L 23/00* (2006.01)

(52) U.S. Cl.
CPC ..... *H01L 21/563* (2013.01); *H01L 2924/01018* (2013.01); *H01L 2224/13099* (2013.01); *H01L 2924/09701* (2013.01); *H01L 2924/01006* (2013.01); *G01L 19/148* (2013.01); *H01L 2924/014* (2013.01); *H01L 24/32* (2013.01); *H01L 2224/16225* (2013.01); *H01L 2924/01057* (2013.01); *H01L 2924/01033* (2013.01); *H01L 2224/26145* (2013.01); *H01L 2224/32225* (2013.01); *H01L 2924/00013* (2013.01)
USPC ........... 257/415; 257/414; 257/678; 257/778; 257/E23.001; 257/E23.003; 257/E23.01; 438/48; 438/49; 438/51; 438/106; 438/108

(58) Field of Classification Search
USPC .................. 257/414, 415, 678, 778, E23.001, 257/E23.003, E23.01, E29.324; 438/48, 49, 438/51, 106, 108
See application file for complete search history.

(56) References Cited

U.S. PATENT DOCUMENTS 6,140,144 A    10/2000  Najafi et al.
6,690,569 B1   2/2004   Mayer et al.

(Continued)

FOREIGN PATENT DOCUMENTS

| DE | 19810060 | 11/1998 |
|---|---|---|
| DE | 19852967 | 5/2000 |
| DE | 102005037948 | 2/2007 |
| WO | WO 9802741 | 12/1996 |

OTHER PUBLICATIONS

M.E. Poplawski, R.W. Hower, and R.B. Brown, "A Simple Packaging Process for Chemical Sensors", Solid-State Sensor and Actuator Workshop, Hilton Head, South Carolina, Jun. 13-16, 1994.

(Continued)

*Primary Examiner* — Peniel M Gumedzoe
(74) *Attorney, Agent, or Firm* — Cooper & Dunham LLP

(57) ABSTRACT

The sensor assembly comprises a substrate (1), such as a flexible printed circuit board, and a sensor chip (2) flip-chip mounted to the substrate (1), with a first side (3) of the sensor chip (2) facing the substrate (1). A sensing area (4) and contact pads (5) are integrated on the first side (3) of the sensor chip (2) and located in a chamber (17) between the substrate (1) and the sensor chip (2). Chamber (17) is bordered along at least two sides by a dam (16). Underfill (18) and/or solder flux is arranged between the sensor chip (2) and the substrate (1), and the dam (16) prevents the underfill from entering the chamber (17). An opening (19) extends from the chamber to the environment and is located between the substrate (1) and the sensor chip (2) or extends through the sensor chip (2).

17 Claims, 3 Drawing Sheets

(56) References Cited

U.S. PATENT DOCUMENTS

| | | | |
|---|---|---|---|
| 7,028,531 | B2 | 4/2006 | Nikolaus |
| 7,038,321 | B1* | 5/2006 | Chavan et al. ............... 257/778 |
| 2004/0259329 | A1 | 12/2004 | Boyle et al. |
| 2005/0104186 | A1 | 5/2005 | Yang et al. |
| 2006/0177349 | A1 | 8/2006 | Thaysen et al. |
| 2007/0275495 | A1 | 11/2007 | Mayer et al. |
| 2008/0250847 | A1 | 10/2008 | Kitani et al. |
| 2012/0217593 | A1 | 8/2012 | Graf et al. |
| 2012/0267731 | A1 | 10/2012 | Graf et al. |

OTHER PUBLICATIONS

C Li, F.E. Sauser, R.G. Azizkhan, C.H. Ahn and I. Papautsky, "Polymer flip-chip bonding of pressure sensors on a flexible Kapton film for neonatal catheters", J. Micromech. Microeng. 15 (2005) 1729-1735.

Communication from the Examining Division issued on Apr. 2, 2013 by the European Patent Office in connection with European Patent Application No. 09756135.1.

R. Fillion, Advanced Packaging Technology for Leading Edge Microelectronics and Flexible Electronics, MSE 542, Cornell University.

International Search Report in PCT/CH2009/000367.

"Thermal CMOS Anemometers, A Thesis submitted to the Swiss Federal Institute of Technology Zurich for the degree of Doctor of Natural Causes", presented by Felix Mayer 1998, Abstract p. 5, Zusammenfassung p. 7, 6.2 Flip-Chip as a Sensor Packaging Technology, p. 75.

* cited by examiner

SENSOR MOUNTED IN FLIP-CHIP TECHNOLOGY ON A SUBSTRATE

TECHNICAL FIELD

The invention relates to a sensor assembly comprising a substrate and a sensor chip flip-chip mounted to the substrate as well as to a method for manufacturing such a sensor.

BACKGROUND ART

Flip-chip mounting of sensor chips to substrates allows for a simple and efficient manufacturing of sensor assemblies, such as e.g. described in WO 98/27411, where a sensor chip having a sensing area integrated on a first side thereof is mounted to a substrate. The sensing area is structured to measure at least one parameter of the environment, such as environmental humidity or pressure, and has therefore to be accessible. For this reason, a window of the substrate is arranged opposite to the sensing area. Contact pads integrated on the first side of the sensor chip can be used to establish electrical contacts between the sensor chip and the substrate during flip-chip mounting.

Typically, and also as shown in WO 98/27411, the gap between the sensor chip and the substrate is filled by a filler material, the so-called "underfill". The underfill is typically applied as a liquid to one or two edges of the sensor chip after flip-chip mounting, and the liquid is then drawn into the gap using capillary forces and it is subsequently hardened.

In order to prevent the underfill from covering the sensing area, the sensor assembly of WO 98/27411 is provided with a dam extending around the sensing area and the window. Similar dams can be useful for preventing solder flux from covering the sensing area. When flip-chip mounting the sensor chip to the substrate, care must be taken to properly align the window in the substrate, the dam and the sensing area.

DISCLOSURE OF THE INVENTION

The problem to be solved by the present invention is to provide an assembly of the type mentioned above that can be manufactured easily.

This problem is solved by the sensor assembly of claim 1. Accordingly, the assembly comprises a dam extending between the sensor chip and the substrate. A chamber is formed between the sensor chip, the substrate and the dam, with the sensing area being located at least partially in this chamber. The dam is arranged between the contact section (i.e. the region where the contact pads are arranged on the sensor chip) and the chamber, thereby forming a barrier between the underfill or solder fulx and the sensing area. Further, at least one opening is provided extending from the chamber to the environment around the sensor assembly. This opening can extend between the substrate and the sensor chip, or it can extend through the sensor chip.

The invention also relates to a method for manufacturing this type of sensor comprising the steps of flip-chip mounting the sensor chip to said substrate, and
 applying said underfill or solder flux between said contact section and said substrate, with said dam being arranged between said underfill or solder flux and said sensing area.

In contrast to a conventional solution where the sensing area has to be located over an opening extending through the substrate, the invention uses an opening extending through the dam and/or the sensor chip, thereby obviating the need to provide an opening in the substrate and to align the sensor chip with this opening. This simplifies the manufacturing process.

The invention can advantageously be used for applications where costs are to be kept low, such as in consumer electronics devices and computer equipment, such as hard disk drives.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

The sensor chip:

The sensor assembly described below comprises a sensor chip with a sensing area integrated thereon. The sensor chip is advantageously a semiconductor chip, but it may e.g. also be a glass or ceramics chip. Semiconductor chips have the advantage that they allow for direct integration of further circuitry thereon.

The sensing area can e.g. comprise a humidity sensor and/or a pressure sensor. It is e.g. formed by a flexible membrane of a pressure sensor or a moisture adsorbing material and a set of electrodes in the case of a humidity sensor.

A pressure sensor can e.g. be structured as disclosed in EP 1 860 418, the disclosure of which is incorporated herein by reference. In particular, the present invention is especially suited for absolute pressure sensors.

A humidity sensor can e.g. be structured as disclosed in U.S. Pat. No. 6,690,569, the disclosure of which is incorporated herein by reference.

As e.g. described in U.S. Pat. No. 6,690,569, in addition to a sensing area and contact pads, the sensor chip may also have further elements integrated thereon, in particular passive and active circuitry, such as amplifiers, filters, A/D- or D/A-converters, digital processing circuitry, etc.

The substrate:

The assembly described below further comprises a substrate. The substrate is typically a printed circuit board having conducting leads mounted thereon. Advantageously, the substrate is a flexible printed circuit board. The term "flexible printed circuit board" refers to an electrically insulating substrate that has circuit leads integrated thereon and that can be reversibly bent to a radius of 1 cm or smaller.

FIRST EMBODIMENT

Figure 1:
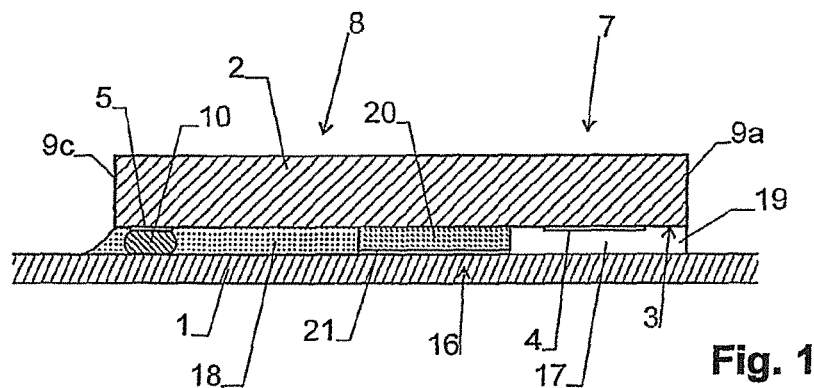
FIG. 1 shows a sectional view of a first sensor assembly.
Figure 2:
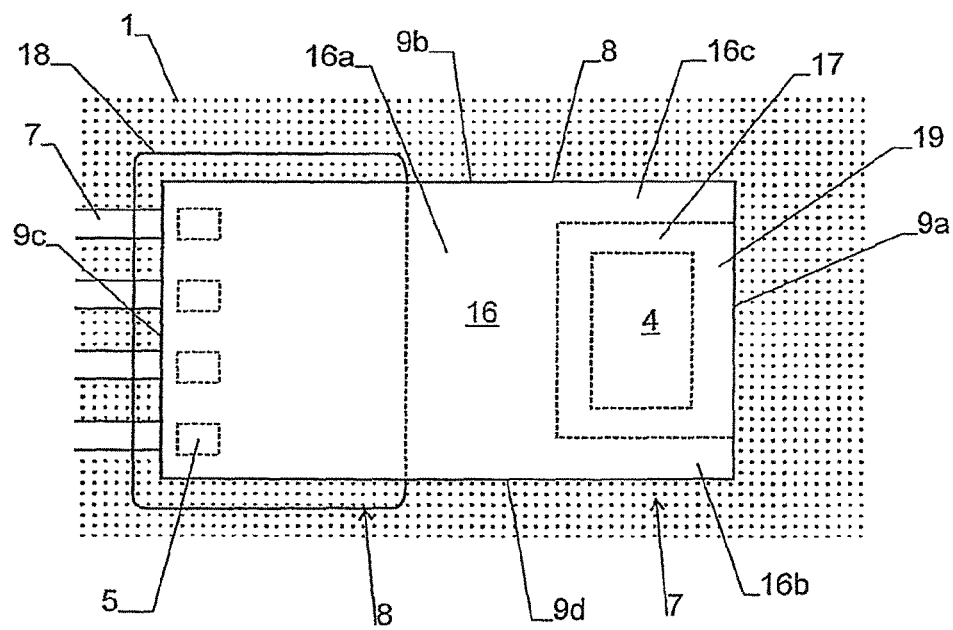
FIG. 2 shows a top view of the sensor assembly of FIG. 1.
Figure 9:
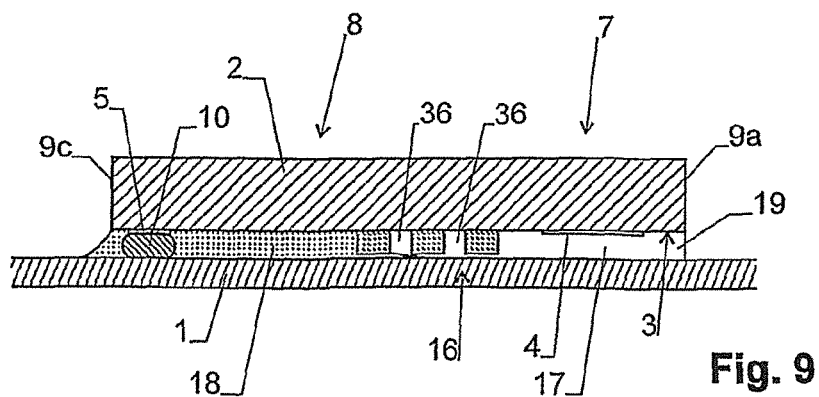
FIG. 9 shows a sectional view of a fifth sensor assembly.

FIGS. 1 and 2 show a sensor assembly according to a first embodiment of the invention. It comprises a substrate 1 and a sensor chip 2 as described above. Sensor chip 2 is flip-chip mounted to substrate 1, with a first side 3 of sensor chip 2 facing substrate 1.

The sensing area 4 and the contact pads 5 are both integrated on first side 3 of sensor chip 2, together with any further components integrated on sensor chip 2. Sensing area 4 is arranged in a first section of substrate 1, in the following called the "sensing section 7", while the contact pads 5 are arranged in a second section of substrate 1, in the following called the "contact section 8".

The contact pads 5 are electrically connected to conducting leads 7 on substrate 1 by means of solder bumps 10 as it is known to the skilled person.

Sensor chip 2 is substantially rectangular having a first lateral edge 9a at the end side of sensing section 7, a second lateral edge 9b extending perpendicular to first lateral edge 9a, a third lateral edge 9c at an end side of contact section 8 and extending perpendicular to second lateral edge 9b, and a fourth lateral edge 9d extending perpendicular to third lateral edge 9c.

The sensor assembly comprises a dam 16 arranged as a layer extending between sensor chip 2 and substrate 1. In the embodiment of FIGS. 1 and 2, dam 16 is substantially U-shaped having a base 16a, which extends between second lateral edge 9b and fourth lateral edge 9d, and legs 16b, 16c, which extend from base 16a along fourth lateral edge 9d and second lateral edge 9b, respectively. Dam 16 encloses a chamber 17 formed between sensor chip 2 (forming a top side of chamber 17), substrate 1 (forming a bottom side of chamber 17) and dam 16 (forming three of four lateral sides of chamber 17). At one lateral side (left hand side in FIGS. 1 and 2) an opening 19 is provided in chamber 17. Opening 19 is arranged between substrate 1, sensor chip 2 and the legs 16b, 16c and extends from a first edge 9a of sensor chip 2 through dam 16 to chamber 17.

Sensing area 4 is located at least partially in chamber 17 and communicates with the environment through opening 19.

The underfill 18 is arranged between sensor chip 2 and substrate 1, namely in contact section 8 of sensor chip 2, and is laterally bordered by dam 16. Dam 16 prevents underfill 18 from entering chamber 17. In order to minimize the risk of underfill 18 entering chamber 17, the legs 16b, 16c of dam 16 advantageously extend all the way to first edge 19a of sensor chip 2, i.e. to the edge where opening 19 is located.

Figure 3:
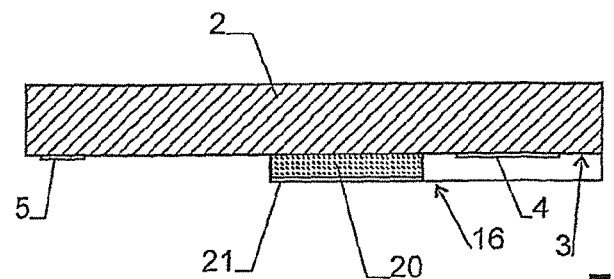
FIG. 3 shows a first manufacturing step of a sensor assembly.
Figure 4:
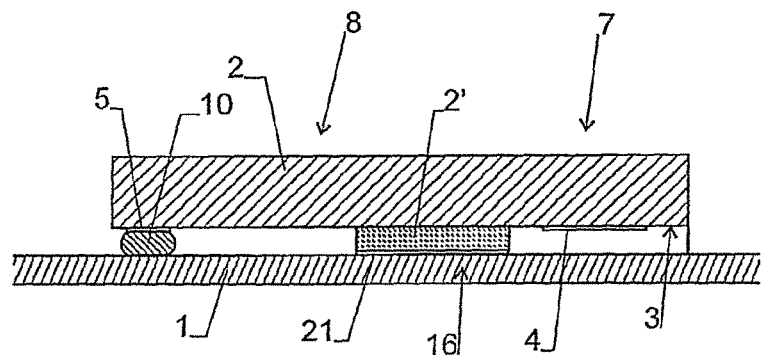
FIG. 4 shows a second manufacturing step of a sensor assembly

FIGS. 3 and 4 show the steps for manufacturing the sensor assembly.

First, sensor chip 2 is provided, with sensing area 4 and contact pads 5 integrated on its first side 3. Next, dam 16 is applied to first side 3. Dam 16 has a height substantially equal to the solder bumps 10 that are formed during the later flip-chip mounting step. It is advantageously formed at least partially of a photoresist, in particular SU-8, thus that it can be structured easily.

The term "photoresist" is to be understood as any material that is structured by irradiation and subsequent selective removal of irradiated or non-irradiated parts.

In the embodiment shown in FIGS. 1-4, dam 16 comprises a first layer 20, which is advantageously formed by the photoresist mentioned above, and a second layer 21, which is advantageously an adhesive for being bonded to substrate 1. First layer 20 extends from sensor chip 2 to second layer 21, and second layer 21 extends, in the final assembly, from first layer 20 to substrate 1.

In a next step, the parts shown in FIG. 3 are flip-chip mounted to substrate 1 and the solder bumps 10 are formed to create the electrical connections between the contact pads 5 and the leads 7. At the same time, dam 16 is bonded to substrate 1, in the embodiment shown here by means of second layer 21. As mentioned, second layer 21 is advantageously an adhesive. For example, it can be applied to either first layer 21 or substrate 1 prior to flip-chip mounting. It may be a glue that bonds upon contact, or it may be a hot-melt adhesive that creates a bond at the elevated temperatures (typically around 260° C.) during flip-chip mounting. Also, layer 21 can be a UV-curable adhesive, which can be cured by UV-irradiation through substrate 1, or a snap-curable adhesive, which can be cured by heating above a threshold temperature.

As mentioned above, the height of dam 16 is advantageously substantially equal to the height of the solder bumps 10 formed during flip-chip mounting such that sensor chip 2 is aligned substantially parallel to substrate 1. Optionally, dam 16 may be of a material that is softened or even liquefied at the temperatures used during flip-chip mounting, which allows to improve this alignment by adjusting the positioning angle of sensor chip 2.

After flip-chip mounting, underfill 18 is applied, in liquid form, along the edge of sensor chip 2 in the region of contact section 8, drawn into the gap between sensor chip 2 and substrate 1, and hardened. As described above, the blocking action of dam 16 prevents underfill 18 from covering sensing area 4.

SECOND EMBODIMENT

Figure 5:
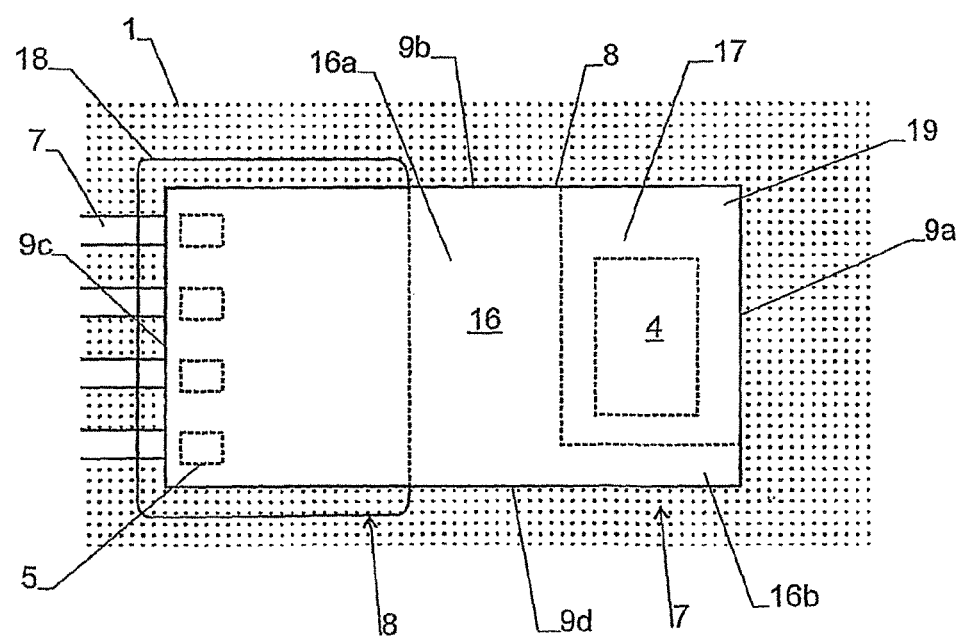
FIG. 5 shows a top view of a second sensor assembly.

FIG. 5 shows a second embodiment of a sensor assembly. The design of the embodiment of FIG. 5 is the same as the one of FIG. 2 and merely differs in the shape of dam 16. While dam 16 of the embodiment of FIG. 2 is U-shaped, dam 16 of FIG. 5 is substantially L-shaped having a base 16a, which extends between second lateral edge 9b and fourth lateral edge 9d, and a leg 16b, which extends from base 16a along fourth lateral edge 9d to first lateral edge 9a. Hence, in this embodiment, chamber 17 is open towards first lateral edge 9a and second lateral edge 9b. In other words, opening 19 of chamber 17 extends from first lateral edge 9a and second lateral edge 9b through dam 16.

This embodiment provides better communication of chamber 17 with the environment because opening 19 has a larger diameter. Since underfill is typically applied along two edges of a chip, this sensor design is still compatible with conventional underfilling techniques as long as the underfill is applied from third and fourth edge 9c, 9d only.

In a further embodiment (not shown) leg 16b of dam 16 can be dispensed with, in which case chamber 17 is open on three sides. In that case, care must be taken to insert underfill 18 only at the side of dam 16 that faces away from chamber 17.

THIRD EMBODIMENT

Figure 6:
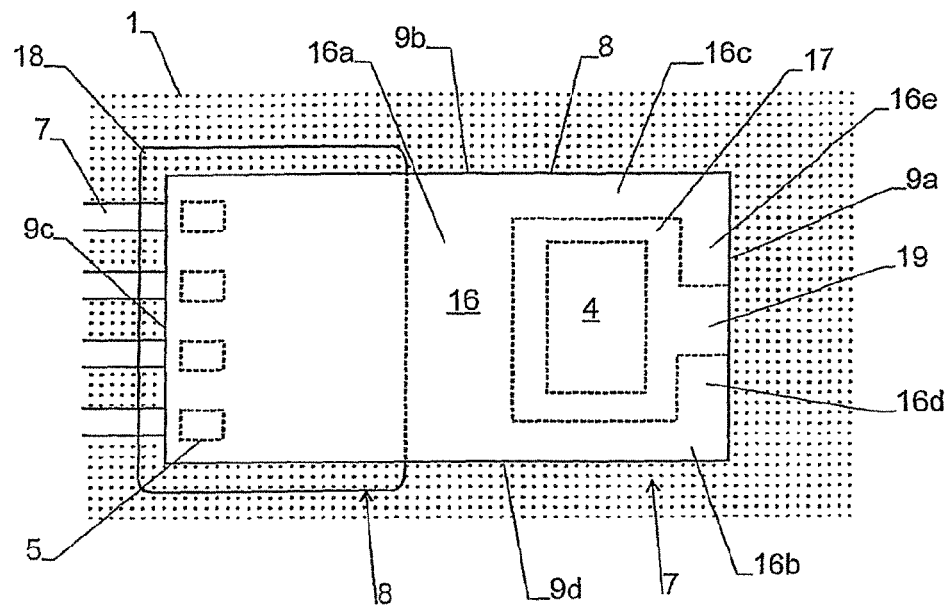
FIG. 6 shows a top view of a third sensor assembly.

FIG. 6 shows a third embodiment. It again differs from the embodiment of FIG. 2 in the shape of dam 16 in that the legs 16b and 16c have bent sections 16d and 16e at their ends. The bent sections 16d, 16e extend inwards along first edge 9a, thereby narrowing the diameter of opening 19. This design lessens the risk of underfill 18 or any other foreign bodies entering chamber 17.

FOURTH EMBODIMENT

Figure 7:
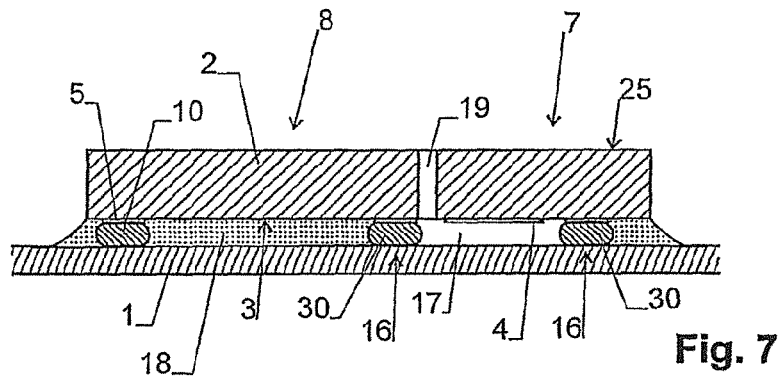
FIG. 7 shows a sectional view of a fourth sensor assembly.
Figure 8:
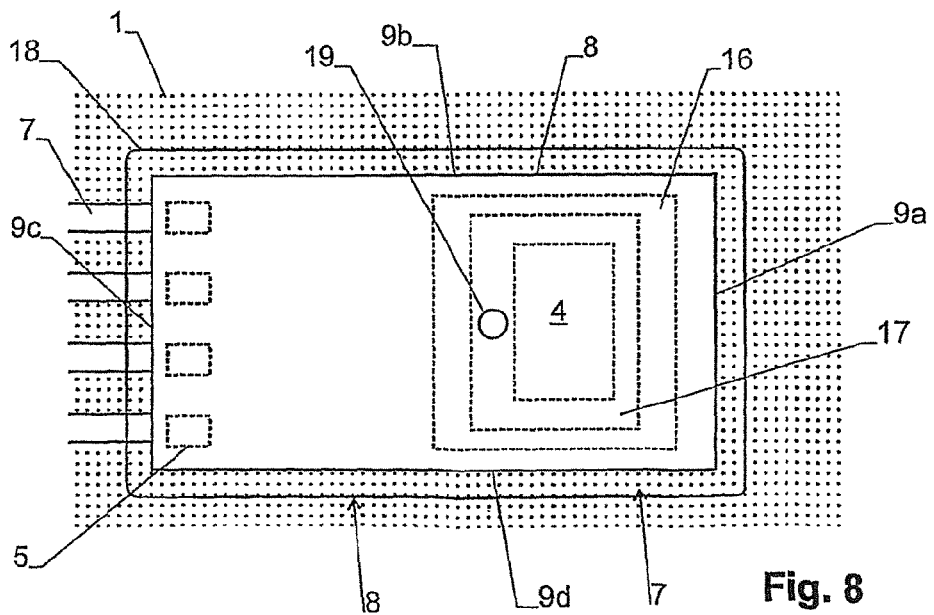
FIG. 8 shows a top view of the sensor assembly of FIG. 7.

The embodiment of FIGS. 7 and 8 differs from the one of FIG. 2 in three aspects.

A first difference lies in the fact that dam 16 is formed by solder, advantageously by a bump 30 extending all the way around chamber 17 and therefore sensing area 4. It seals chamber 17 against underfill 18. It must be noted, though, that this fourth embodiment does not necessarily require a dam made of solder, but may also use a dam as described in reference to FIG. 3, and vice versa.

A second difference lies in the fact that opening 19 is not arranged between substrate 1 and sensor chip 2 but rather extends through sensor chip 2 to the second side 25 of sensor chip 2, with second side 25 being opposite first side 3.

A third possible difference lies in the fact that dam 16 does not extend to the edges of sensor chip 2, but rather ends at a distance therefrom, such that a gap is formed for receiving underfill 18 all around sensor chip 2, thereby improving the attachment of sensor chip 2 to substrate 1.

In the embodiment of FIGS. 7 and 8, opening 19 can be manufactured e.g. using anisotropic etching or laser drilling. Techniques for laser drilling semiconductor wafers are known to the skilled person and are e.g. described in EP 1 677 346, the disclosure of which is incorporated herein by reference.

FIFTH EMBODIMENT

The embodiment differs from the one of FIG. 1 in that the underside of dam 16, i.e. the side facing substrate 1, comprises one or more recessed sections or gaps 36 that extend parallel to the dam 16. In that case, even if a small gap remains between the underside of dam 16 and substrate 1, underfill 18 may enter a first recess or gap 36, but will generally stop there. Hence, such recessed sections or gaps 36 allow to improve the sealing properties of dam 16 and can even obviate the need to fixedly connect dam 16 to substrate 1.

Notes

In the embodiments described above, underfill 18 has been arranged between sensor chip 2 and substrate 1, at least in the region of contact section 8. As mentioned, though, the dam can also be used to prevent solder flux, which is applied with the solder, from entering sensing area 4. Hence, the invention is also useful for sensor assemblies that do not use underfill.

The present invention simplifies the manufacturing process of a sensor assembly because it allows to use conventional flip-chip mounting and does not rely on any opening in substrate 1 to be arranged at the location of chamber 17. In fact, and as shown in the figures, substrate 1 can be closed at the location of chamber 17.

Typically, dam 16 is arranged between sensing section 7 and contact section 8 of sensor chip 2, with sensing area 4 being arranged on a first side thereof and contact pads 5 being arranged at an opposite, second side thereof, such that the contact section 8 can be filled with underfill 18.

While there are shown and described presently preferred embodiments of the invention, it is to be distinctly understood that the invention is not limited thereto but may be otherwise variously embodied and practiced within the scope of the following claims.

The invention claimed is:

1. A sensor assembly comprising:
   a substrate,
   a sensor chip flip-chip mounted to said substrate with a first side of said sensor chip facing said substrate,
   a sensing area integrated on the first side of said sensor chip, wherein said sensing area is structured to measure at least one parameter,
   contact pads integrated on the first side of said sensor chip in a contact section of said sensor chip, wherein said contact pads are electrically connected to said substrate,
   a dam extending between said sensor chip and said substrate, wherein a chamber is formed between said sensor chip, said substrate, and said dam, with said sensing area being located at least partially in said chamber and with said dam being arranged between said contact section and said chamber, and
   at least one opening extending from said chamber to an environment around said sensor assembly, wherein said opening is arranged between said substrate and said sensor chip or extends through said sensor chip, and wherein said dam comprises solder.

2. The sensor assembly of claim 1 further comprising an underfill arranged in said contact section between said sensor chip and said substrate, wherein said dam is arranged between said underfill and said sensing area.

3. The sensor assembly of claim 1 wherein said opening is arranged between said substrate and said sensor chip and extends from at least a first edge of said sensor chip to said chamber.

4. The sensor assembly of claim 3 wherein said dam extends to said first edge.

5. The sensor assembly of claim 1 wherein said substrate is a flexible printed circuit board.

6. The sensor assembly of claim 1 wherein said substrate is closed at said chamber.

7. The sensor assembly of claim 1 wherein said sensing area comprises a humidity sensor and/or a pressure sensor.

8. The sensor assembly of claim 1 wherein said sensing area is arranged at a first side of said dam and said contact pads are arranged at a second, opposite side of said dam.

9. A method for manufacturing the sensor assembly of claim 1 comprising the steps of
   flip-chip mounting said sensor chip to said substrate, and
   applying underfill or solder flux between said contact section and said substrate, with said dam being arranged between said underfill or solder flux and said sensing area.

10. The method of claim 9 comprising the step of applying said dam to the first side of said sensor chip prior to flip-chip mounting said sensor chip.

11. The method of claim 9, wherein said dam is adhesively bonded to said substrate using a clue, a hot-melt adhesive, a UV-curable adhesive, or a snap-curable adhesive.

12. A sensor assembly comprising:
   a substrate,
   a sensor chip flip-chip mounted to said substrate with a first side of said sensor chip facing said substrate,
   a sensing area integrated on the first side of said sensor chip, wherein said sensing area is structured to measure at least one parameter,
   contact pads integrated on the first side of said sensor chip in a contact section of said sensor chip, wherein said contact pads are electrically connected to said substrate,
   a dam extending between said sensor chip and said substrate, wherein a chamber is formed between said sensor chip, said substrate, and said dam, with said sensing area being located at least partially in said chamber and with said dam being arranged between said contact section and said chamber, and
   at least one opening extending from said chamber to an environment around said sensor assembly, wherein said opening is arranged between said substrate and said sensor chip and extends from at least a first edge of said sensor chip to said chamber, wherein said dam extends to said first edge, and wherein said opening extends from said first edge and a second edge of said sensor chip to said chamber and wherein said dam extends to said first edge and said second edge, wherein said first edge is adjacent to said second edge.

13. A sensor assembly comprising:

a substrate, a sensor chip flip-chip mounted to said substrate with a first side of said sensor chip facing said substrate, a sensing area integrated on the first side of said sensor chip, wherein said sensing area is structured to measure at least one parameter, contact pads integrated on the first side of said sensor chip in a contact section of said sensor chip, wherein said contact pads are electrically connected to said substrate, a dam extending between said sensor chip and said substrate, wherein a chamber is formed between said sensor chip, said substrate, and said dam, with said sensing area being located at least partially in said chamber and with said dam being arranged between said contact section and said chamber, and at least one opening extending from said chamber to an environment around said sensor assembly, wherein said opening is arranged between said substrate and said sensor chip and extends from at least a first edge of said sensor chip to said chamber, wherein said dam extends to said first edge, and wherein said dam comprises a base extending from a second edge to a fourth edge of said sensor chip, a first leg extending from said base along said fourth edge of said sensor chip to said first edge of said sensor chip, and a second leg extending from said base along said second edge of said sensor chip to said first edge of said sensor chip, and wherein said opening is formed between said first and second legs.

14. The sensor assembly of claim 13 wherein said dam comprises a photoresist, in particular SU-8.

15. The sensor assembly of claim 13 wherein said dam comprises a first layer and a second layer, wherein said first layer extends from said sensor chip and wherein said second layer extends to said substrate, wherein said second layer is an adhesive.

16. A sensor assembly comprising:

a substrate, a sensor chip flip-chip mounted to said substrate with a first side of said sensor chip facing said substrate, a sensing area integrated on the first side of said sensor chip, wherein said sensing area is structured to measure at least one parameter, contact pads integrated on the first side of said sensor chip in a contact section of said sensor chip, wherein said contact pads are electrically connected to said substrate, a dam extending between said sensor chip and said substrate, wherein a chamber is formed between said sensor chip, said substrate, and said dam, with said sensing area being located at least partially in said chamber and with said dam being arranged between said contact section and said chamber, at least one opening extending from said chamber to an environment around said sensor assembly, wherein said opening extends through said sensor chip, and an underfill arranged in said contact section between said sensor chip and said substrate, wherein said dam is arranged between said underfill and said sensing area, and wherein said dam extends sealingly around said chamber.

17. A sensor assembly comprising:

a substrate, a sensor chip flip-chip mounted to said substrate with a first side of said sensor chip facing said substrate, a sensing area integrated on the first side of said sensor chip, wherein said sensing area is structured to measure at least one parameter, contact pads integrated on the first side of said sensor chip in a contact section of said sensor chip, wherein said contact pads are electrically connected to said substrate, a dam extending between said sensor chip and said substrate, wherein a chamber is formed between said sensor chip, said substrate, and said dam, with said sensing area being located at least partially in said chamber and with said dam being arranged between said contact section and said chamber, and at least one opening extending from said chamber to an environment around said sensor assembly, wherein said opening is arranged between said substrate and said sensor chip or extends through said sensor chip, and wherein said dam comprises one or more recesses or gaps extending in a single layer of said dam.

\* \* \* \* \*